United States Patent [19]

Butler et al.

[11] Patent Number: 4,530,929
[45] Date of Patent: Jul. 23, 1985

[54] BENZOTRICYCLIC NITROGEN-CONTAINING DIONES AND THEIR USE IN REVERSING ELECTROCONVULSIVE SHOCK-INDUCED AMNESIA

[75] Inventors: Donald E. Butler; Michael R. Pavia; Fred M. Hershenson, all of Ann Arbor, Mich.

[73] Assignee: Warner-Lambert Company, Morris Plains, N.J.

[21] Appl. No.: 576,242

[22] Filed: Feb. 2, 1984

[51] Int. Cl.$^3$ .................. C07D 455/00; C07D 471/02
[52] U.S. Cl. ..................................... 514/295; 546/95; 546/99
[58] Field of Search ................ 546/95, 99; 424/258; 514/295

[56] References Cited

U.S. PATENT DOCUMENTS 4,115,555 7/1977 Wade et al. ........................ 546/99

FOREIGN PATENT DOCUMENTS 0079162 5/1983 European Pat. Off. ............. 546/95

*Primary Examiner*—Henry R. Jiles
*Assistant Examiner*—P. Ann Bucci
*Attorney, Agent, or Firm*—Jerry F. Janssen

[57] ABSTRACT

A class of novel fused-ring, benzotricyclic, nitrogen-containing diones useful as agents in reversing electroconvulsive shock-induced amnesia. A method of preparing the compounds, pharmaceutical compositions including the compounds, and a method of reversing electroconvulsive shock-induced amnesia are disclosed.

16 Claims, No Drawings

BENZOTRICYCLIC NITROGEN-CONTAINING DIONES AND THEIR USE IN REVERSING ELECTROCONVULSIVE SHOCK-INDUCED AMNESIA

CROSS-REFERENCE TO RELATED APPLICATIONS

This application relates to subject matter disclosed and claimed in co-pending application Ser. No. 576,232 filed concurrently herewith and assigned to the present assignee.

BACKGROUND OF THE INVENTION

The present invention relates to compounds and pharmaceutical compositions useful in the reversal of electroconvulsive shock-induced amnesia. More particularly, it is concerned with certain benzotricyclic nitrogen-containing diones, with a method of preparing such compounds, pharmaceutical compositions including these compounds, and a method of reversing electroconvulsive shock-induced amnesia.

SUMMARY AND DETAILED DESCRIPTION

In its broadest aspect, the present invention relates to compounds having the structural formula I:

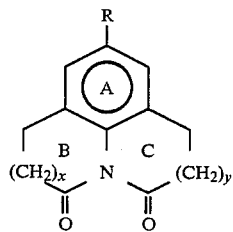

wherein x, and y are independently zero or one, with the proviso that x and y may not both be zero, and R is hydrogen; halogen; hydroxyl; —$OR_1$ where $R_1$ is alkyl of from one to six carbon atoms, phenyl, or benzyl; or —$NR_2R_3$ where $R_2$ and $R_3$ are alkyl of from one to six carbon atoms.

Compounds of the present invention, represented by structure I, comprise a class of structurally related tricyclic fused-ring nitrogen-containing dione compounds in which one of the fused rings is a substituted or unsubstituted aromatic carbocyclic ring, and the other two rings are saturated lactam rings. The present invention contemplates compounds where rings B and C (as indicated above) may independently be five- or six-membered rings. It is believed, however, that ring strain prevents closure of both lactam rings B and C when both are five-membered rings.

Although structurally similar, the nomenclature of the class of compounds encompassed by the present invention is somewhat complex. The names of the compounds are based in part on the names of the corresponding unsaturated nitrogen-containing fused ring systems.

The aromatic carbocyclic ring (A as indicated in the structure above) may either be unsubstituted or is mono-substituted, preferably at the position indicated in structure I, with halogen, hydroxyl, alkoxyl of from one to six carbon atoms, phenoxyl, phenylmethoxyl, or dialkylamino where the alkyl group is of from one to six carbon atoms.

The exact conformation of compounds of the present invention is not known with certainty at the time of filing of this application; however, rings B and C may be "puckered" (i.e., nonplanar), leading to stereoisomerism. In addition, stereoisomerism may be introduced into the structures of compound I by the presence of asymmetric centers in R where R is alkyl, alkoxyl, and dialkylamino. The present invention contemplates all stereoisomers of the generic structural formula I shown above.

The terms "stereoisomers" and "stereoisomerism" as used throughout this specification and the appended claims are to be given the meaning usually ascribed to them by practitioners of the organic chemical arts, and specifically as defined by Eliel in "Stereochemistry of Carbon Compounds," pp 1-6, McGraw-Hill, New York, 1962.

The term "alkyl of from one to six carbon atoms" as used herein contemplates branched and unbranched hydrocarbon groupings containing one to six carbon atoms as, for example, methyl, ethyl, n- and isopropyl, n-, sec-, iso-, and tert-butyl, n-, iso-, sec-, and neopentyl, n-, sec-, and iso-hexyl, etc.

Examples of compounds falling within the scope of the present invention include, but are not necessarily limited to, the following compounds and their stereoisomers.

5,6-Dihydro-4H-pyrrolo[3,2,1-ij]quinoline-2,4(1H)-dione.

1,2,6,7-Tetrahydro-3H,5H-benzo[ij]quinolizine-3,5-dione.

8-Fluoro-5,6-dihydro-4H-pyrrolo[3,2,1-ij]quinoline-2,4(1H)-dione.

9-Chloro-1,2,6,7-tetrahydro-3H,5H-benzo[ij]quinolizine-3,5-dione.

8-Bromo-5,6-dihydro-4H-pyrrolo[3,2,1-ij]quinoline-2,4(1H)-dione.

9-Methoxy-1,2,6,7-tetrahydro-3H,5H-benzo[ij]quinolizine-3,5-dione.

8-Phenoxy-5,6-dihydro-4H-pyrrolo[3,2,1-ij]quinoline-2,4(1H)-dione.

9-Hydroxy-1,2,6,7-tetrahydro-3H,5H-benzo[ij]quinolizine-3,5-dione.

8-Phenylmethoxy-5,6-dihydro-4H-pyrrolo[3,2,1-ij]quinoline-2,4(1H)-dione.

9-Dimethylamino-1,2,6,7-tetrahydro-3H,5H-benzo[ij]quinolizine-3,5-dione.

The compounds of this invention are prepared by cyclizing a compound having the structural formula Ia

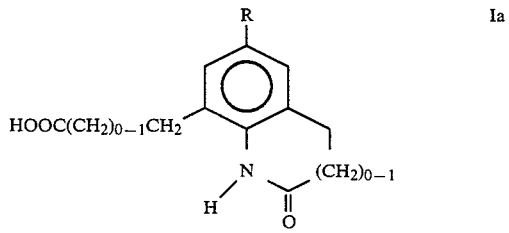

to compounds having structural formula I by heating with a cyclizing agent selected from the group of carboxylic acid anhydrides such as acetic anhydride, propanoic anhydride, benzoic anhydride, etc., aroyl sulfonyl halides such as benzenesulfonyl chloride, p-toluenesulfonyl chloride and the like, or alkylsulfonyl halides such as methanesulfonyl chloride. Particularly preferred as a cyclizing reagents for this reaction are the compounds benzyl chloroformate or acetic anhydride.

The reaction is preferably carried out by heating the compounds of structure Ia with the cyclizing agent in the presence of an acid acceptor such as tertiary amine. A preferred catalyst is 4-dimethylaminopyridine (4-DAP).

Those compounds of formula I where either x or y is one and the other designator is zero (i.e., those compounds in which one of the lactam rings is six-membered and the other is five-membered) are prepared by the general reaction sequence illustrated in Reaction Scheme 1.

The known 4-substituted-2-methylanilines (II) are converted to the corresponding 5-substituted-7-methylisatins (III) by the reaction described in A. Wahl, et al, *Ann. Chim.*, 5:314 (1926). The 5-chloro-7-methylisatin [H. Pajouhesh et al, *J. Pharm. Sci.*, 72 (3), 381–421 (1983)] and the 5-bromo-7-methylisatin [German Offenlegungschrift DE 2925175] are known compounds. The methyl group of the isatin, III, is subsequently photocatalytically halogenated by reaction with, for example, bromine under ultraviolet light in the inert solvent such as dichloromethane containing a trace amount of water, to produce the 5-substituted-7-bromomethylisatin (IV).

Reaction of the 7-bromomethylisatin with the sodio derivative of dimethylmalonate in, for example, tetrahydrofuran at 0° C. produces the diester, compound V. Saponification in dilute aqueous base results in decarboxylation of compound V to produce, after acidification, the monocarboxylic acid compound VI. Reduction of compound VI by hydrogen over, for example, platinum/carbon catalyst yields the lactam VII which cyclizes to the benzotricyclic product VIII in the presence of hot acetic anhydride.

Those compounds of formula I where both x and y are one (i.e., those compounds in which both lactam rings are six-membered) are prepared by the general reaction sequence illustrated in Reaction Scheme 2.

The 4-substituted-2,6-dimethylnitrobenzene compounds of formula IX, where Y is hydrogen, fluorine, chlorine, or bromine, are oxidized, for example by hot, aqueous, basic permanganate solution to the corresponding substituted isophthalic acid derivatives, X. These compounds are subsequently reduced, for example, by borane-tetrahydrofuran complex to the 4-substituted-2,6-bis(hydroxymethyl)-nitrobenzene compounds of formula XI. The hydroxymethyl groups are oxidized to the corresponding aldehyde groups by a mild oxidizing reagent such as pyridinium chlorochromate, and the aldehydes are converted to the diesters, XII, by the well-known Wittig Reaction [c.f. U. Schöollkopf, *Angew. Chem.*, 71:260 (1959)].

In the specific instance where Y is fluorine, the fluoronitro diesters of formula XII are converted to compounds of formula XIII where Z is alkoxyl of from one to six carbon atoms, phenoxyl, phenylmethoxyl, or dialkylamino of from one to six carbon atoms by reaction with the appropriate alcohol or dialkylamine in dimethylforamide in the presence of potassium carbonate.

Catalytic reduction of the resulting compounds by hydrogen reduces both the nitro group and the carbon-carbon unsaturation and cyclizes one lactam ring to produce compounds of formula XIV. Where R is halogen, the nitro group is reduced using Fe and HCl. Saponification of the ester, XIV, in dilute base followed by acidification produces the acid, which is cyclized to the substituted benzotricyclic product XV in hot acetic anhydride.

Reaction Scheme 1

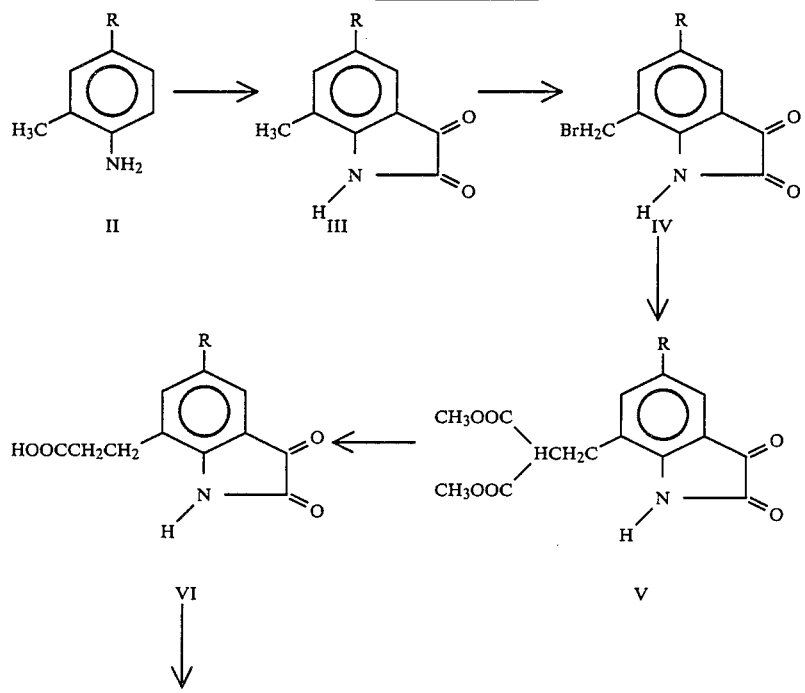

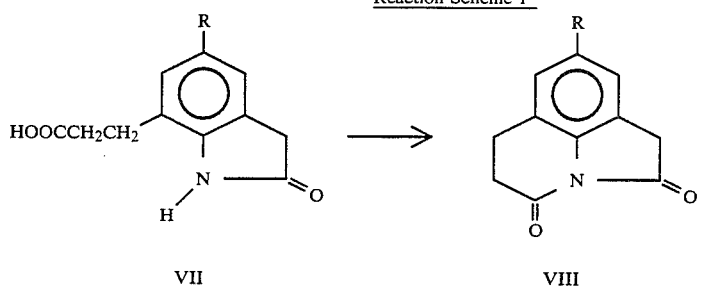
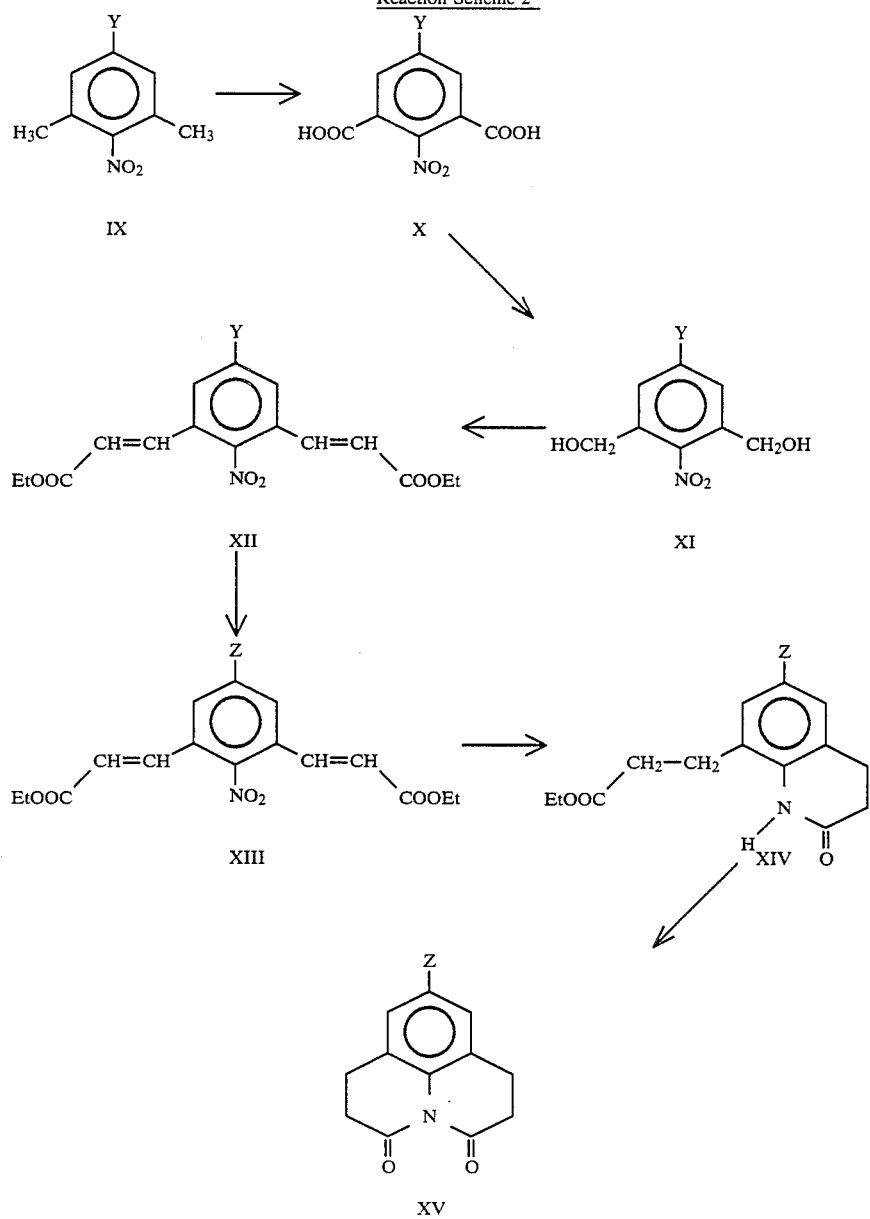

Also in accordance with the present invention, pharmaceutical compositions may be produced by formulating compounds having structural formula I above in unit dosage form with a pharmaceutically acceptable carrier. Some examples of unit dosage forms are tablets, capsules, lozenges, and pills; as well as powders and aqueous and nonaqueous solutions and suspensions packaged in containers containing either one, or some larger number of dosage units and capable of being subdivided into individual doses by such means as measurement into a teaspoon or other standard container.

Some examples of suitable pharmaceutical carriers, including pharmaceutical diluents, are sugars such as lactose and sucrose; starches such as corn starch and potato starch; cellulose derivatives such as sodium carboxymethylcellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerin; sorbitol; polyethylene glycol; water; agar; alginic acid; as well as other compatible substances normally employed in pharmaceutical formulations.

The pharmaceutical compositions of this invention can also contain other components such as coloring agents, flavoring agents, and/or preservatives. These latter materials, if present, are generally used in relatively small amounts. The compositions can, if desired, also contain other therapeutic agents, including other cognition activating agents such as 3-phenoxypyridine, and N-[N'N'-diisopropylaminoethyl]pyrrolidine-2-oxo-1-acetamide.

The percentage of active ingredient in the foregoing compositions can be varied within wide limits, but for practical purposes, the active ingredient is preferably present in a concentration of a least 10% in a solid composition, and at least 2% in a primarily liquid composition. The most satisfactory compositions are those in which a much higher proportion of the active ingredient is present. The pharmaceutical compositions of this invention contain from 0.1 to 250.0 mg, preferably from 1 to 25 mg of the active ingredient per dosage unit so that the entire amount to be administered during a day can be made from a reasonable number of dose units.

The compounds of the present invention may exist as solids in anhydrous form as well as forms which are solvated with water, alcohols, and other pharmaceutically acceptable solvents. These solid forms may be incorporated into formulations intended for parenteral administration. Such formulations may be either in solution form or in powdered form intended for combination with an isotonic solution containing other ingredients such as preservatives, etc.

The solid forms of the compounds of this invention may also be incorporated into suppository formulations intended for rectal administration or into syrup formulations intended for oral administration.

The mammalian dose range for a 70 kg subject is from 1 to 1500 mg of compound per day, preferably between about 25 mg to 750 mg per day, optionally administered in portions.

The compounds of the present invention are useful for reversing electroconvulsive shock-induced amnesia. The effectiveness of these compounds was evaluated by a test designed to show the ability of a given substance to reverse amnesia induced by electroconvulsive shock. The test is more fully described in U.S. Pat. No. 4,154,347, issued Mar. 20, 1979, and incorporated herein by reference. The only differences between the tests conducted in the present case and that described in the referenced patent were that in the present case, the test compounds were administered orally and the duration of the electrical shock used to induce amnesia in the test animals was 1.0 second.

The data from tests conducted employing compounds of the present invention appear in the Table I.

The following criteria were used in interpreting the data: 40% or more amnesia reversal in the test animals = active, A; 25% to 39% amnesia reversal = borderline activity, C; 0% to 24% reversal of amnesia = inactive, N.

TABLE I

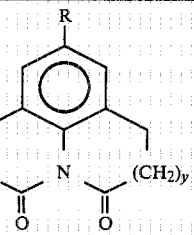

Percent Amnesia Reversal of Orally Administered Test Compounds (In Mice)

| Compound | x | y | R | Dose (mg/kg of Body Weight) | | |
|---|---|---|---|---|---|---|
| | | | | 100 | 10 | 1 |
| 1 | 0 | 1 | H | 85(A) | 62(1) | 31(C) |

A modification of the test referenced above was employed to test another compound in accordance with the present invention against standard laboratory rats.

This test assesses the ability of novel chemical entities to reverse retrograde amnesia produced by electroconvulsive shock treatment in rats. Activity in this test is presumed to be indicative of potential cognition activating activity in human patients with impaired cognitive function.

Fifty weanling male rats (Charles River, CD strain, 21 days old at time of shipment) are randomly divided into five groups of ten rats each. Rats are placed individually into a highly illuminated box (6×8 inch) which opens onto a darkened chamber (12×8 inch) with electrified grids. Rats move freely from the illuminated compartment to the darkened chamber through a door (4×4 inch). When the rat has all four feet within the darkened chamber, the floor of the darkened box is electrified (0.58 ma) and the rat is shocked until it exits to the original illuminated area. If the rat reenters the darkened box before one minute elapses it again receives a foot shock until it exits to the illuminated area. When the rat remains in the illuminated area for one minute, it is removed and placed in a group holding cage.

Two hours after the above training the rats are given a single electroconvulsive shock produced by a 20 ma shock delivered for 1.0 seconds through the corneas. Immediately thereafter, the rats are returned to the holding cage.

Two hours after the electroconvulsive treatment, the rats are administered the test chemical orally (injected intraperitoneally, or intramuscularly for special tests). Usually three doses of the chemical will be tested at a time, and usually these doses will be 1, 10, and 100 mg/kg.

One hour after drug treatment, the rats are tested for retention of the avoidance response. This testing is accomplished by again placing each rat in the illuminated area adjoining the shock box. Any rat that remains in the illuminated area and does not enter the darkened box for 60 seconds is counted as retaining (remembering) the avoidance response. Any rat entering the box within the 60-second period is counted as having amnesia for the trained response.

Using the 60-second criterion described above, appropriate control experiments showed the following: First, upon retest all rats entered the box if no foot shock was delivered during the original training. This shows that the painful foot shock was necessary for the rats to develop an aversion to entering the test box. Second, few animals receiving foot shock not followed by ECS entered the darkened chamber when tested five hours after training, indicating that they remembered the painful training experience and were inhibited from entering the darkened chamber. Third, the majority of rats entered the box under the foregoing conditions when treated with electroconvulsive shock two hours after training. This indicates that the electroconvulsive shock treatment itself does not induce a fear of entering the test box and produces an amnesia for the painful training experienced three hours earlier.

The five groups of rats are treated as follows:

| Group | Treatments | |
|---|---|---|
| Baseline Control Group | ECS, | Placebo |
| Ceiling Control Group | —, | Placebo |
| First Drug Dose Group | ECS, | Drug |
| Second Drug Dose Group | ECS, | Drug |
| Third Drug Dose Group | ECS, | Drug |

Before a chemical is evaluated there must be a 50% difference between the baseline control and ceiling control. If the difference between the two control groups is less than 50% the experiment is discarded. This is to ensure that both the training and amnestic treatment are sufficient.

Activity of the drug is be interpreted in the following manner. If the difference between the number of animals in the drug and control groups entering the box is equal to or greater than three, the compound is considered to be significantly active. Therefore, the compound will be rated either active or inactive. Under these conditions, a difference of this magnitude will always be statistically significant using the multinomial expansion of the $\chi^2$ test.

| Rating | Interpretation |
|---|---|
| A | Active |
| N | Inactive |

The results of this test appear in Table II.

TABLE II

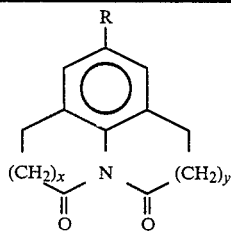

Percent Amnesia Reversal of Orally Administered Test Compound (In Rats)

| Compound | x | y | R | Dose (mg/kg of Body Weight) | | |
|---|---|---|---|---|---|---|
| | | | | 100 | 10 | 1 |
| 2 | 1 | 1 | H | 75(A) | 66(A) | 83(A) |

The following synthetic examples are provided to enable one skilled in the art to practice the present invention. These examples are not to be read as limiting the scope of the invention as it is defined by the appended claims, but merely illustrative thereof.

EXAMPLE 1

Preparation of 7-methylisatin

In a 5 l flask is placed chloral hydrate (90 g, 0.54 mole) and water (1200 ml). To this solution is added sodium sulfate decahydrate (1300 g, 10.9 mole) followed by a solution of o-methylaniline (54 g, 0.5 mole) in water (300 ml) containing concentrated hydrochloric acid (43 ml, 0.5 mole). Then a solution of hydroxylamine hydrochloride (110 g, 1.58 mole) in water (50 ml) is added. The reaction mixture is heated to reflux over a 90 minute period and refluxed 30 minutes. The reaction is cooled in ice and the resulting crystalline ortho-isonitrosoacetotoluidide is isolated by filtration and air dried. The orthoisonitrosoacetotoluidide is dissolved in portions in concentrated sulfuric acid (325 ml) that is preheated to 50° C. with vigorous stirring. The reaction temperature is maintained under 75° C. When the addition is complete, the mixture is heated at 80° C. for 30 minutes, cooled, and poured unto ice (3 kg). The 7-methylisatin is isolated by filtration. The 7-methylisatin is purified by dissolution in dilute sodium hydroxide. The basic solution is treated with 4N hydrochloric acid until a slight amount of precipitation is evident. The mixture is filtered and the filtrate is acidified. The pure 7-methylisatin is recovered by filtration and dried in vacuo at 80° C. and 0.1 mm pressure, mp 114°–145° C. (A. Wahl, et al., Ann. Chim. 5 314 (1926).

Preparation of 7-bromomethylisatin

The 7-methylisatin (16.1 g, 0.1 mole) is suspended in dichloroethane (2000 ml) and the suspension is heated and irradiated with a high intensity light source to the reflux point. Bromine (24.3 g, 0.15 mole) is added dropwise over a one hour period.

The solution is filtered hot and concentrated at reduced pressure to yield the product as an orange solid after washing with anhydrous diethyl ether. The product is purified using flash chromatography on silica (elution with 24:1 dichloromethane:diethyl ether) to afford after drying (at 60° C. at 0.1 mm); 7-bromomethylisatin, mp 199°–200° C. dec.

Preparation of 2,3-dihydro-2,3-dioxo-1H-indole-7-propandioic acid dimethyl ester A solution of dimethylmalonate (15.7 ml, 0.138 mole) in tetrahydrofuran is cooled to 0° C. and sodium hydride (50% in mineral oil) (6.5 g, 0.138 mole) is added portion wise over 15 minutes. The reaction is stirred at 0° C. for 30 minutes and a suspension of 7-bromomethylisatin (15.0 g, 0.0625 mole) in tetrahydrofuran (50 ml) is added in one portion. The resulting deep purple solution is stirred at room temperature for 30 minutes. 1.2N hydrochloric acid is added until the mixture turns clear yellow and the solution is concentrated at reduced pressure to 20% of the original volume. The solution is extracted with dichloromethane (2×300 ml). The combined extracts are dried (MgSO4), filtered, and concentrated to yield a yellow solid. This is purified by flash chromatography on silica (elution with 9:1 dichloromethane:diethyl ether) to afford after concentration pure 2,3-dihydro-2,3-dioxo-1H-indole-7-propandioic acid dimethyl ester, mp 137°–140° C.

Preparation of 2,3-dihydro-2-oxo-1H-indole-7-propandioic acid dimethyl ester

A solution of 2,3-dihydro-2,3-dioxo-1H-indole-7-propandioic acid dimethyl ester (1.4 g, 0.0048 mole) is dissolved in acetic acid (100 ml) and in the presence of 20% Pd/C is treated with hydrogen gas at 50 psi. The solution is filtered and concentrated to yield 2,3-dihydro-2-oxo-1H-indole-7-propandioic acid dimethyl ester. This is purified by flash chromatography on silica (elution with 7:3 hexane: ethyl acetate) to give after concentration pure 2,3-dihydro-2-oxo-1H-indole-7-propandioic acid dimethyl ester, mp 161°–161.5° C.

Preparation of 2,3-dihydro-2-oxo-1H-indole-7-propanoic acid

A solution of 2,3-dihydro-2-oxo-1H-indole-7-propandioic acid dimethyl ester (4.6 g, 0.0166 moles) is dissolved in methanol (50 ml) and 1N sodium hydroxide (33.2 ml, 0.0332 mole) is added. The mixture is stirred at 50° C. for 90 minutes then concentrated at reduced pressure. The residue is dissolved in water (75 ml) and methanol (50 ml). The solution is made acidic with excess Dowex 50X-8 acidic ion exchange resin and heated with stirring at 70° C. for 24 hours. The solution is cooled, filtered, and concentrated to dryness to yield 2,3-dihydro-2-oxo-1H-indole-7-propanoic acid. The 2,3-dihydro-2-oxo-1H-indole-7-propanoic acid is purified by flash chromatography on silica (elution with 9:1 dichloromethane:methanol) NMR spectra: ('H-CDCl$_{13}$) $\delta$ 7.30–7.10 (m, 3H), $\delta$ 6.50–6.25 (b, 1H) $\delta$ 3.80–3.70 (m, 2H), $\delta$ 3.70 (5, 2H), $\delta$ 3.28–3.22 (m, 2H).

Preparation of 5,6-dihydro-4H-pyrrolo[3,2,1-ij]quinoline-2,4(1H)-dione

A solution of 2,3-dihydro-2-oxo-1H-indole-7-propanoic acid (2.0 g, 0.0098 mole) in acetic anhydride (8 ml) is heated to 90° C. with stirring for one hour. Excess acetic anhydride is removed at reduced pressure. The red crystalline material is purified by flash chromatography over silica (elution with 23:2 dichloromethane:diethyl ether). Final purification by fractional sublimation yields 5,6-dihydro-4H-pyrrolo[3,2,1-ij]quinoline-2,4(1H)-dione, mp 194°–197° C.

EXAMPLE 2

Preparation of 2-nitro-1,3-benzenedimethanol 2,6-dimethyl-1-nitrobenzene is oxidized to 2-nitro-1,3-benzenedicarboxylic acid as described by E. Notting and C. Gachot; Chem. Ber., 39, 73–75 (1906) to yield 2-nitro-1,3-benzene dicarboxylic acid.

A solution of 2-nitro-1,3-benzenedicarboxylic acid (12.7 g, 0.06 mole) in tetrahydrofuran (60 ml) is cooled to 0° C. and 1N borane:tetrahydrofuran (300 ml, 0.3 mole) is added dropwise over one hour. The mixture is allowed to warm slowly to 25° C. and is stirred for 36 hours. Methanol (50 ml) is added slowly, the mixture is filtered and evaporated. The residue is dissolved in ethyl acetate (100 ml) and washed with water (25 ml), dried (MgSO$_4$), filtered, and evaporated to yield a yellow solid. This is further purified by flash chromatography over silica (elution with 1:1 hexane:ethyl acetate) to afford after concentration pure 2-nitro-1,3-benzenedimethanol, mp 100°–101° C.

Preparation of 2-nitro-1,3-benzenediacrylic acid diethyl ester

A solution of 2-nitro-1,3-benzenedimethanol (5.0 g, 0.027 mole) in dichloromethane (90 ml) is mixed with anhydrous sodium acetate (10 g). The mixture is cooled to 0° C. and pyridinium chlorochromate (4.0 eq, 21.4 g, 0.1 mole) is added portionwise over 10 minutes. The reaction is allowed to warm to room temperature over six hours. The mixture is poured into diethyl ether (1 l) and filtered through Florosil. The colorless solution is concentrated at reduced pressure and azeotroped with heptane to remove pyridine. The resulting oil is reasonably pure 2-nitro-1,3-benzenedialdehyde and is used as is.

The 2-nitro-1,3-benzenedialdehyde (3.4 g, 0.019 mole) is dissolved in toluene (60 ml) and carbethoxymethylene triphenylphosphorane (19.2 g, 0.06 mole) is added. The mixture is heated at 60° C. for eight hours, cooled, and concentrated at reduced pressure. Diethyl ether (100 ml) is added and the mixture is filtered. The filtrate is concentrated and purified by flash chromatography over silica (elution with 4:1 hexane:ethyl acetate) to afford after concentration pure 2-nitro-1,3-benzenediacrylic acid diethyl ester, mp 114°–115° C.

Preparation of 1,2,3,4-Tetrahydro-2-oxo-8-quinolinepropanoic acid ethyl ester A solution of 2-nitro-1,3-benzenediacrylic acid diethyl ester (3.5 g, 0.011 mole) in absolute ethanol (100 ml) is treated with hydrogen at 1 atmosphere pressure for 12 hours in the presence of 20% Pd/C. The mixture is filtered and concentrated at reduced pressure to yield 1,2,3,4-tetrahydro-2-oxo-8-quinolinepropanoic acid ethyl ester, mp 102°–103° C.

Preparation of 1,2,3,4-tetrahydro-2-oxo-8-quinolinepropanoic acid

A solution of 1,2,3,4-tetrahydro-2-oxo-8-quinolinepropanoic acid ethyl ester (2.5 g, 0.01 mole) in methanol (50 ml) is treated with 0.5N sodium hydroxide solution (19.5 ml, 0.00975 mole) and the mixture is heated at 50° C. for two hours. The mixture is concentrated at reduced pressure to yield the sodium salt of 1,2,3,4-tetrahydro-2-oxo-8-quinolinepropanoic acid as a solid. The sodium salt of 1,2,3,4-tetrahydro-2-oxo-8-quinolinepropanoic acid is dissolved in 2:1 water: methanol (5 ml) and the solution is passed over a Dowex 50X-8 ion exchange column and the solution is concentrated at reduced pressure to yield 1,2,3,4-tetrahydro-2-oxo-8-quinolinepropanoic acid.

Preparation of 1,2,6,7-tetrahydro-3H,5H-benzo[ij]quinolizine-3,5-dione

The 1,2,3,4-tetrahydro-2-oxo-8-quinolinepropanoic acid (2.1 g, 0.0096 mole) is dissolved in acetic anhydride (10 ml) and the solution is heated to 100° C. for one hour. Excess acetic anhydride is removed at reduced pressure and the residual anhydride is removed by addition of toluene and repeated concentration. The solid is recrystallized from ethyl acetate to yield pure 1,2,6,7-tetrahydro-3H,5H-benzo[ij]quinolizine-3,5-dione, mp 136°–140° C.

We claim:

1. A compound having the structural formula I:

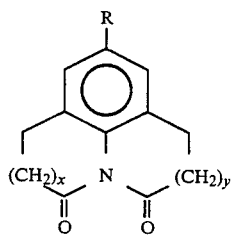

wherein x and y are independently zero or one, with the proviso that x and y many not both be zero, and wherein R is hydrogen, halogen; hydroxyl; —$OR_1$ where $R_1$ is alkyl from one to six carbon atoms, phenyl, or phenylmethyl; or —$NR_2R_3$ where $R_2$ and $R_3$ are alkyl of from one to six carbon atoms.

2. A compound in accordance with claim 1 wherein x is zero and y is one.

3. A compound in accordance with claim 2 wherein x and y are both one.

4. A compond in accordance with claim 2 having the name 5,6-Dihydro-4H-pyrrolo[3,2,1-ij]quinoline-2,4(1H)dione.

5. A compound in accordance with claim 3 having the name 1,2,6,7-Tetrahydro-3H,5H-benzo[ij]quinolizine-3,5-dione.

6. A compound in accordance with claim 2 having the name 8-Fluoro-5,6-dihydro-4H-pyrrolo[3,2,1-ij]quinoline2,4(1H)-dione.

7. A compound in accordance with claim 3 having the name 9-Chloro-1,2,6,7-tetrahydro-3H,5H-benzo[ij]-quinolizine-3,5-dione.

8. A compound in accordance with claim 2 having the name 8-Bromo-5,6-dihydro-4H-pyrrolo[3,2,1-ij]quinoline 2,4(1H)-dione.

9. A compound in accordance with claim 3 having the name 9-Methoxy-1,2,6,7-tetrahydro-3H,5H-benzo[ij]quinolizine-3,5-dione.

10. A compound in accordance with claim 2 having the name 8-Phenoxy-5,6-dihydro-4H-pyrrolo[3,2,1-ij]quinoline-2,4(1H)-dione.

11. A compound in accordance with claim 3 having the name 9-Hydroxy-1,2,6,7-tetrahydro-3H,5H-benzo[ij]quinolizine-3,5-dione.

12. A compound in accordance with claim 2 having the name 8-Phenylmethoxy-5,6-dihydro-4H-pyrrolo[3,2,1-ij]quinoline-2,4(1H)-dione.

13. A compound in accordance with claim 3 having the name 9-Dimethylamino-1,2,6,7-tetrahydro-3H,5H-benzo[ij]quinolizine-3,5-dione.

14. A method of preparing a compound having the structural formula:

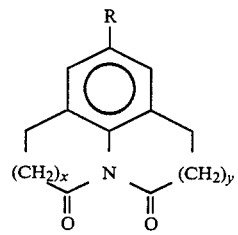

wherein x, and y are independently zero or one, with the proviso that x and y may not both be zero, and R is hydrogen; halogen; hydroxyl; —$OR_1$ where $R_1$ alkyl of from one to six carbon atoms, phenyl, or benzyl; or —$NR_2R_3$ where $R_2$ and $R_3$ are alkyl of from one to six carbon atoms, said process comprising reacting compound of the formula

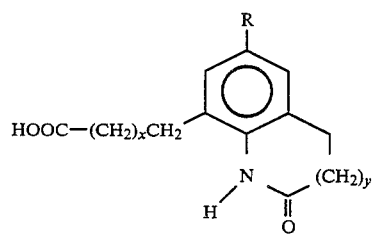

wherein x, y, and R are defined above, with a cyclizing reagent selected from the group consisting of carboxylic acid anhydrides, aroyl sulfonyl halides, and alkylsulfonyl halides, and chlorobenzyl formate in the presence of an acid acceptor.

15. A composition for reversing the effects of electroconvulsive shock-induced amnesia comprising an amnesia reversing effective amount of a compound in accordance with claim 1 in combination with a pharmaceutically acceptable carrier.

16. A method for reversing electroconvulsive shock-induced amnesia in mammals comprising administering to a mammal in need of such treatment an effective amount of a composition in accordance with claim 15.

* * * * *